(12) United States Patent
Culbert et al.

(10) Patent No.: US 11,918,255 B2
(45) Date of Patent: *Mar. 5, 2024

(54) ADJUSTABLE MAGNETIC DEVICES AND METHODS OF USING SAME

(71) Applicant: NuVasive Specialized Orthopedics, Inc., San Diego, CA (US)

(72) Inventors: Brad Culbert, Rancho Santa Margarita, CA (US); Scott Pool, Laguna Hills, CA (US); Blair Walker, Mission Viejo, CA (US); Arvin Chang, Yorba Linda, CA (US); Peter P. Tran, Irvine, CA (US)

(73) Assignee: Nuvasive Specialized Orthopedics Inc., San Diego, CA (US)

( * ) Notice: Subject to any disclaimer, the term of this patent is extended or adjusted under 35 U.S.C. 154(b) by 171 days.

This patent is subject to a terminal disclaimer.

(21) Appl. No.: 17/352,485

(22) Filed: Jun. 21, 2021

(65) Prior Publication Data

US 2021/0307787 A1    Oct. 7, 2021

Related U.S. Application Data

(60) Division of application No. 16/297,257, filed on Mar. 8, 2019, now Pat. No. 11,123,107, which is a
(Continued)

(51) Int. Cl.
*A61B 17/70* (2006.01)
*A61B 17/86* (2006.01)
(Continued)

(52) U.S. Cl.
CPC ...... *A61B 17/7016* (2013.01); *A61B 17/7002* (2013.01); *A61B 17/7037* (2013.01);
(Continued)

(58) Field of Classification Search
CPC ......... A61B 17/7016; A61B 17/7014–17/7031
See application file for complete search history.

(56) References Cited

U.S. PATENT DOCUMENTS 2,702,031 A    2/1955  Wenger
3,111,945 A   11/1963  Von Solbrig
(Continued)

FOREIGN PATENT DOCUMENTS

CN    1697630 A    11/2005
CN  101040807 A     9/2007
(Continued)

OTHER PUBLICATIONS

Abe et al., "Experimental external fixation combined with percutaneous discectomy in the management of scoliosis.", SPINE, 1999, pp. 646-653, 24, No. 7.
(Continued)

*Primary Examiner* — Julianna N Harvey

(57) ABSTRACT

A system includes a first pedicle screw, a second pedicle screw, and an adjustable rod having an outer housing coupled to one of the first pedicle screw and the second pedicle screw, the outer housing having a threaded shaft secured to one end thereof extending along an interior portion thereof. The system further includes a hollow magnetic assembly disposed within the outer housing and having a magnetic element disposed therein, the hollow magnetic assembly having an internal threaded surface engaged with the threaded shaft, the magnetic assembly being coupled to the other of the first pedicle screw and the second pedicle screw, wherein the hollow magnetic assembly rotates in response to an externally applied magnetic field to thereby lengthen or shorten the distance between the first pedicle screw and the second pedicle screw.

19 Claims, 12 Drawing Sheets

Related U.S. Application Data continuation of application No. 14/449,761, filed on Aug. 1, 2014, now Pat. No. 10,265,101, which is a continuation of application No. 14/301,238, filed on Jun. 10, 2014, now Pat. No. 10,349,982, which is a continuation of application No. 14/355,202, filed as application No. PCT/US2012/062696 on Oct. 31, 2012, now Pat. No. 10,016,220.

(60) Provisional application No. 61/567,936, filed on Dec. 7, 2011, provisional application No. 61/554,389, filed on Nov. 1, 2011.

(51) Int. Cl.
*A61F 2/44* (2006.01)
*A61B 17/00* (2006.01)
*A61B 17/68* (2006.01)

(52) U.S. Cl.
CPC ...... *A61B 17/7046* (2013.01); *A61B 17/7071* (2013.01); *A61B 17/863* (2013.01); *A61B 17/8685* (2013.01); *A61F 2/44* (2013.01); *A61B 2017/00212* (2013.01); *A61B 2017/00876* (2013.01); *A61B 2017/681* (2013.01); *A61B 17/7008* (2013.01)

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,261,913 A | 11/1993 | Marnay |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,273,914 B1 | 8/2001 | Papas |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |

(56) References Cited

U.S. PATENT DOCUMENTS

| | | |
|---|---|---|
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,780,706 B2 | 8/2010 | Marino et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |

(56) References Cited

U.S. PATENT DOCUMENTS

| | | |
|---|---|---|
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 10,265,101 B2 * | 4/2019 | Culbert ............... A61B 17/7002 |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2004/0260283 A1 | 12/2004 | Wu et al. |
| 2005/0034705 A1 | 2/2005 | McClendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0270813 A1 | 11/2007 | Garamszegi |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1* | 11/2007 | Harrison ............... A61B 17/70 606/309 |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |

(56) References Cited

U.S. PATENT DOCUMENTS

| | | |
|---|---|---|
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112207 A1 | 4/2009 | Walker et al. |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0256681 A1 | 10/2010 | Hammer et al. |
| 2010/0256771 A1 | 10/2010 | Roberts et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0137347 A1* | 6/2011 | Hunziker ............ A61B 17/7216 606/259 |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | WO2007013059 A3 | 2/2007 |
| WO | WO2007015239 A3 | 2/2007 |
| WO | WO2011116158 A3 | 9/2011 |
| WO | WO2013119528 A1 | 8/2013 |
| WO | WO2014040013 A1 | 3/2014 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

(56) References Cited

OTHER PUBLICATIONS

Boudjemline et al., "Off-label use of an adjustable gastric banding system for pulmonary artery banding.", The Journal of Thoracic and Cardiovascular Surgery, 2006, pp. 1130-1135, 131, No. 5.
Brown et al., "Single port surgery and the Dundee Endocone.", SAGES Annual Scientific Sessions: Emerging Technology Poster Abstracts, 2007, ETP007, pp. 323-324.
Buchowski et al., "Temporary internal distraction as an aid to correction of severe scoliosis", J Bone Joint Surg Am, 2006, pp. 2035-2041, 88-A, No. 9.
Burghardt et al., "Mechanical failure of the Intramedullary Skeletal Kinetic Distractor in limb lengthening.", J Bone Joint Surg Br, 2011, pp. 639-643, 93-B, No. 5.
Burke, "Design of a minimally invasive non fusion device for the surgical management of scoliosis in the skeletally immature", Studies in Health Technology and Informatics, 2006, pp. 378-384, 123.
Carter et al., "A cumulative damage model for bone fracture.", Journal of Orthopaedic Research, 1985, pp. 84-90, 3, No. 1.
Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", SPINE, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid PortTM system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.

(56) References Cited

OTHER PUBLICATIONS

Matthews et al., "Magnetically adjustable intraocular lens.", Journal of Cataract and Refractive Surgery, 2003, pp. 2211-2216, 29, No. 11.
Micromotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work ?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", SPINE, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", SPINE, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.

\* cited by examiner

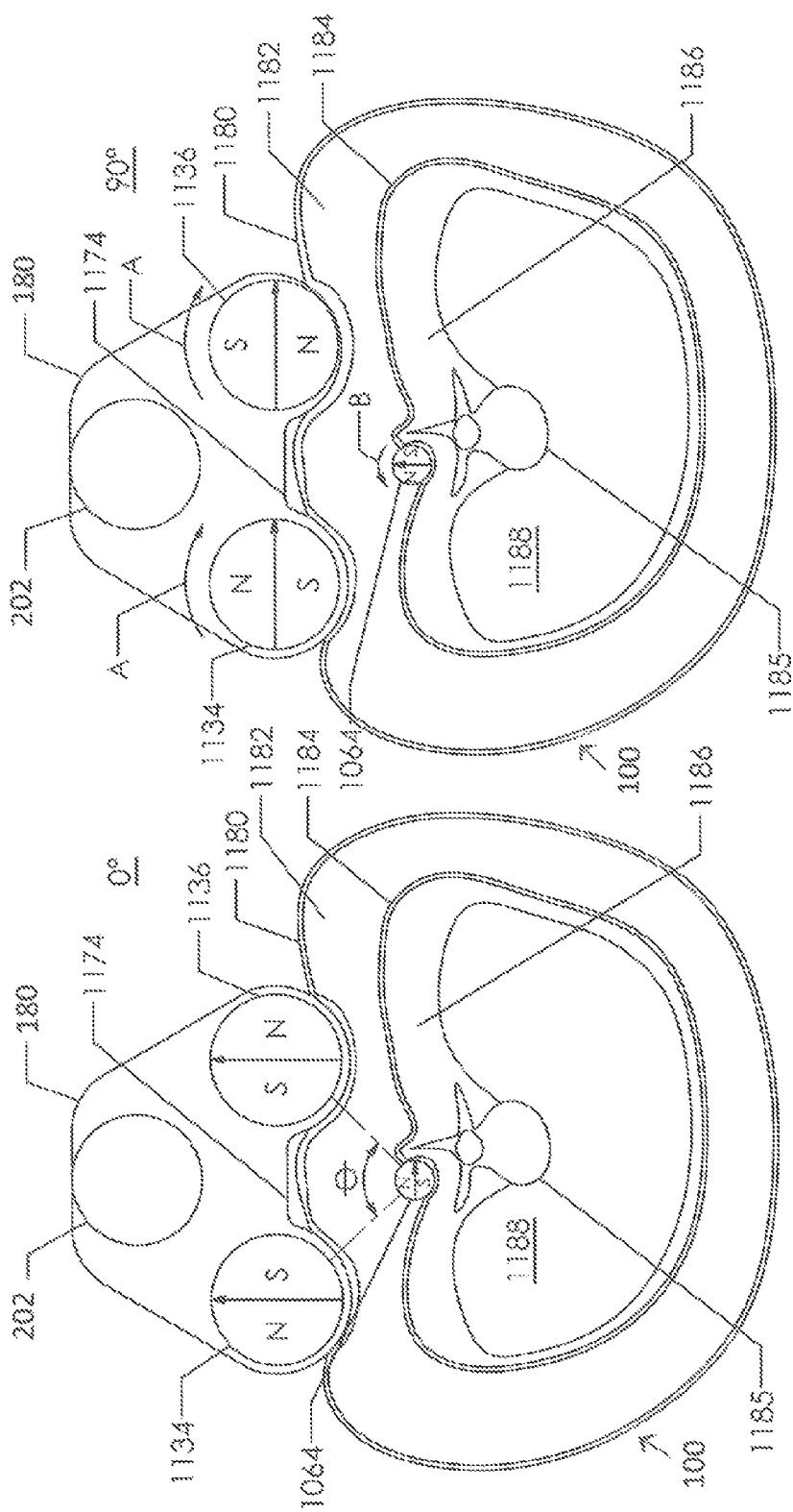

ADJUSTABLE MAGNETIC DEVICES AND METHODS OF USING SAME

RELATED APPLICATIONS

The present application is a divisional of U.S. patent application Ser. No. 16/297,257, filed Mar. 8, 2019, which is a continuation of U.S. patent application Ser. No. 14/449,761, filed Aug. 1, 2014 (now U.S. Pat. No. 10,265,101, issued Apr. 23, 2019), which is a continuation of U.S. patent application Ser. No. 14/301,238, filed Jun. 10, 2014 (now U.S. Pat. No. 10,349,982, issued Jul. 16, 2019), which is a continuation of U.S. patent application Ser. No. 14/355,202, filed Apr. 29, 2014 (now U.S. Pat. No. 10,016,220, issued Jul. 10, 2018), which is a US national stage entry under 35 USC 371 of international patent application no. PCT/US2012/062696, filed Oct. 31, 2012, which claims the benefit of U.S. provisional patent application No. 61/567,936, filed Dec. 7, 2011 and U.S. provisional application No. 61/554,389, filed Nov. 1, 2011. Any and all applications for which a foreign or domestic priority claim is identified above and/or in the Application Data Sheet as filed with the present application are hereby incorporated by reference under 37 CFR 1.57.

FIELD OF THE INVENTION

The field of the invention generally relates to medical devices for treating spinal conditions.

BACKGROUND OF THE INVENTION

Degenerative disc disease affects 65 million Americans. Up to 85% of the population over the age of 50 will suffer from back pain each year. Degenerative disc disease (DDD) is part of the natural process of growing older. Unfortunately as we age, our intervertebral discs lose their flexibility, elasticity, and shock absorbing characteristics. The ligaments that surround the disc, called the annulus fibrosis, become brittle and they are more easily torn. At the same time, the soft gel-like center of the disc, called the nucleus pulposus, starts to dry out and shrink. The combination of damage to the intervertebral discs, the development of bone spurs, and a gradual thickening of the ligaments that support the spine can all contribute to degenerative arthritis of the lumbar spine.

When degenerative disc disease becomes painful or symptomatic, it can cause several different symptoms, including back pain, leg pain, and weakness that are due to compression of the nerve roots. These symptoms are caused by the fact that worn out discs are a source of pain because they do not function as well as they once did, and as they shrink, the space available for the nerve roots also shrinks. As the discs between the intervertebral bodies start to wear out, the entire lumbar spine becomes less flexible. As a result, people complain of back pain and stiffness, especially towards the end of the day.

Depending on the severity and the condition, there are many ways to treat DDD patients, with fusion being the most common surgical option. The estimated number of thoracolumbar fixation procedures in 2009 was 250,000. Surgery for degenerative disc disease usually involves removing the damaged disc. In some cases, the bone is then permanently joined or fused to protect the spinal cord. There are many different techniques and approaches to a fusion procedure. Some of the most common are ALIFs, PLIFs, TLIFs, XLIFs (lateral), etc. Almost all of these techniques now involve some sort of interbody fusion device supplemented with posterior fixation (i.e., 360 fusion).

Another spinal malady that commonly affects patients is stenosis of the spine. Stenosis is related to the degeneration of the spine and typically presents itself in later life. Spinal stenosis can occur in a variety of ways in the spine. Most of the cases of stenosis occur in the lumbar region (i.e., lower back) of the spine, although stenosis is also common in the cervical region of the spine. Central stenosis is a choking of the central canal that compresses the nerve tissue within the spinal canal. Lateral stenosis occurs due to the trapping or compression of nerves after it has left the spinal canal. This can be caused by bony spur protrusions, bulging, or herniated discs.

SUMMARY OF THE INVENTION

In one embodiment, a system includes a first pedicle screw, a second pedicle screw, and an adjustable rod having an outer housing coupled to one of the first pedicle screw and the second pedicle screw, the outer housing having a threaded shaft secured to one end thereof extending along an interior portion thereof The system further includes a hollow magnetic assembly disposed within the outer housing and having a magnetic element disposed therein, the hollow magnetic assembly having an internal threaded surface engaged with the threaded shaft, the magnetic assembly being coupled to the other of the first pedicle screw and the second pedicle screw, wherein the hollow magnetic assembly rotates in response to an externally applied magnetic field to thereby lengthen or shorten the distance between the first pedicle screw and the second pedicle screw.

In another embodiment, a method for adjusting the amount of compression between two vertebral bodies includes securing a first pedicle screw to a first vertebra, securing a second pedicle screw to a second vertebra, and securing an adjustable rod between the first pedicle screw and the second pedicle screw, the adjustable rod having an outer housing coupled to the first pedicle screw, the outer housing having a threaded shaft secured to one end thereof extending along an interior portion thereof, the adjustable rod further having a hollow magnetic assembly disposed within the outer housing and having a magnetic element disposed therein, the hollow magnetic assembly having an internal threaded surface engaged with the threaded shaft, the magnetic assembly being coupled to the second pedicle screw. The method further includes applying an external magnetic field to the adjustable rod to rotate the magnetic element.

In another embodiment, a system includes a first pedicle screw having a shank and a head, a second pedicle screw having a shank and a head, and a rod placed between the first pedicle screw and the second pedicle screw and contained within a housing. The system further includes a magnetic actuator disposed within the housing and associated with one of the first and second pedicle screws, the magnetic actuator having a rotatable magnetic clement coupled to a bushing, the rotatable magnetic clement configured to move relative to the housing in response to an externally applied magnetic field, wherein movement in a first direction frictionally engages the rod between the pedicle screw head and the bushing and wherein movement in a second direction disengages the rod from the pedicle screw head and the bushing.

In another embodiment, a system includes a first pedicle screw, a second pedicle screw, and a flexible spacer configured for placement between the first and second pedicle screws, the flexible spacer configured to adjust a compression or tension force between the first pedicle screw and second pedicle screw in response to an externally applied magnetic field.

In another embodiment, a device includes an interbody screw having first and second portions, the first portion having a threaded end and the second portion having a threaded end, at least one of the first and second portions being axially moveable with respect to the other in response to an externally applied magnetic field.

In another embodiment, an artificial disc device includes a body portion, a first adjustable member, and a second adjustable member arranged generally orthogonal to the first adjustable member, where the first and second adjustable members are configured to adjust a COR of the body portion in two orthogonal dimensions in response to an externally applied magnetic field.

In another embodiment, a distraction device interposed between two vertebral bodies includes first and second portions, one of the portions including a permanent magnet configured to rotate in response to an externally applied non-invasive magnetic field, the permanent magnet operatively coupled to a screw whereby rotation in one direction increases the height between the first and second portions.

In another embodiment, a distraction device implanted in a single vertebral body includes first and second portions, one of the portions including a permanent magnet configured to rotate in response to an externally applied non-invasive magnetic field, the permanent magnet operatively coupled to a screw whereby rotation in one direction increases the width between the first and second portions.

In another embodiment, a method of adjusting the spinal canal includes forming first and second bores into a vertebral body, making pedicle cuts to separate a portion of the vertebral body from the pedicles, and securing first and second distraction devices within the first and second bores. The method further includes applying a non-invasive magnetic field to the first and second distraction devices to expand the spinal canal.

In another embodiment, a system for adjusting the spinal canal includes a drilling tool for drilling first and second bores into a vertebral body, a cutting tool for making first and second pedicle cuts to separate a portion of the vertebral body from associated pedicles, and first and second distraction devices configured for placement within the first and second bores. The system further includes an external adjustment device configured to apply a non-invasive magnetic field to the first and second distraction devices, whereby the non-invasive magnetic field distracts both the first and second distraction devices.

BRIEF DESCRIPTION OF THE DRAWINGS

FIG. 15 illustrates a first orientation of two magnets of the external adjustment device in relation to an implanted magnet.

FIG. 16 illustrates a second orientation of the two magnets of the external adjustment device in relation to the implanted magnet.

DETAILED DESCRIPTION OF THE ILLUSTRATED EMBODIMENTS

Figure 1A:
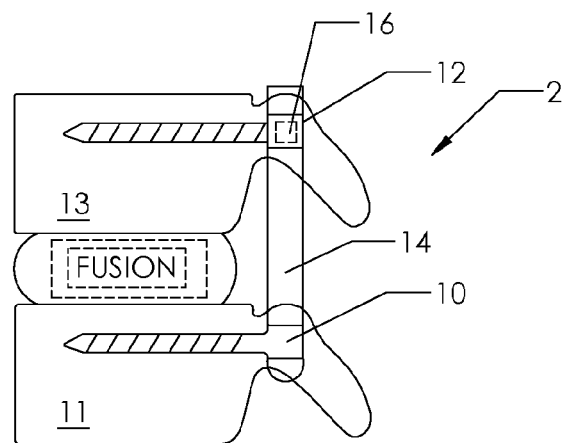
FIG. 1A illustrates one embodiment of a pedicle screw system for fusion.
Figures 1B, 2B:
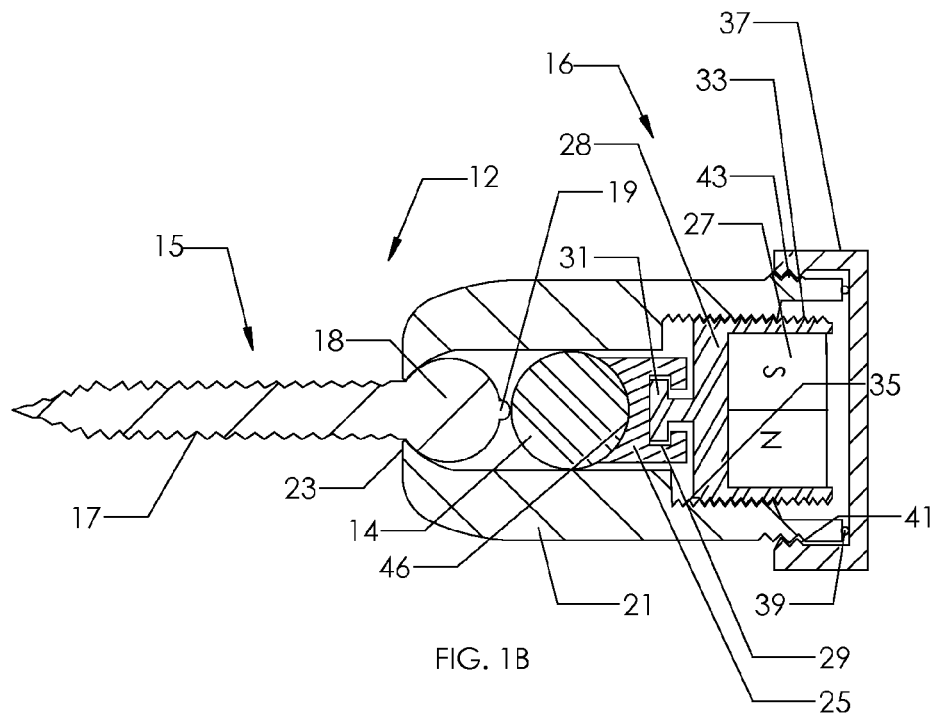
FIG. 1B illustrates a sectional view of a pedicle screw of the pedicle screw system of FIG. 1A.
FIG. 2B illustrates a sectional view of the pedicle screw system of FIG. 2A.

FIG. 1A illustrates a side view of a pedicle screw-based system 2 for the stabilization of the spine during fusion. The device includes a first pedicle screw 10 disposed in a first vertebral body 11, a second pedicle screw 12 disposed in a second vertebral body 13, and a rod 14 located between the first pedicle screw 10 and the second pedicle screw 12. The rod 14 is fixedly secured at one end to the first pedicle screw 10. The opposing end of the rod 14 is selectively coupled/de-coupled to the second pedicle screw 12 using a magnetic actuator 16, seen in more detail in FIG. 1B. The second pedicle screw 12 includes a screw body 15 having a shank 17 and a spherical head 18. Spherical head 18 has a contact surface 19 which serves as a point of contact when the second pedicle screw 12 is coupled to the rod 14. As seen in FIG. 1B, the system 2 includes a housing 21 having an end or lip 23 for engaging with the spherical head 18 of the screw body 15 and maintaining the screw body 15 in a particular orientation in relation to the housing 21 when the second pedicle screw 12 is coupled to the rod 14. The system 2 includes a magnetic element 28 having a radially-poled magnet 27 bonded within the magnetic element 28. One end of the magnetic element 28 has a coupler 31 which fits into a cavity 29 of a bushing 25. The bushing 25 has a saddle-shaped surface 46 that is shaped to engage with a side surface of the rod 14. The magnetic element 28 can rotate freely with respect to the bushing 25, but the coupler 31 transfers axial movement of the magnetic clement 28 to axial movement of the bushing 25 when the coupler 31 makes contact with the bushing 25 inside the cavity 29. The magnetic element 28 includes male threads 33 that engage with corresponding female threads 35 located within an inner surface of the housing 21. As seen in FIG. 1B, the magnetic actuator actuates in a direction that is generally perpendicular to the axis of the rod 14. In this manner, the rod 14 is pinched between the bushing 25 and the head 18 of the pedicle screw 12.

The magnetic actuator 16 can be selectively mechanically engaged or disengaged to the second pedicle screw 12 using an externally applied moving magnetic field. For example, one or more rotating or cycling magnets disposed outside the body can be used to selectively engage or disengage the rod 14 to the second pedicle screw 12 by pinching the rod 14 between the bushing 25 and the contact surface 19 of the spherical head 18 of the second pedicle screw 12. The radially-poled magnet 27 may be made from a rare earth magnet, for example, Neodymium-Iron-Boron. Because the radially-poled magnet 27 and, thus, magnetic element 28 are non-invasively rotated by the moving magnetic field, the bushing 25 is moved axially to frictionally grip the rod 14 between the contact surface 19 of the spherical head 18 and the bushing 25. A cap 37 having female threads 41 is screwed over male threads 43 of the housing 21 to protect the inner contents. As seen in FIG. 1B, an O-ring seal 39 seals the cap 37 to the housing 21. For example, after a fusion procedure has been performed to fuse vertebral bodies 11, 13 together, the subject undergoes radiographic imaging. At this point, the second pedicle screw 12 is engaged with the rod 14. Once evidence of anterior fusion is seen, an external magnetic field is applied (e.g., rotating magnetic field) to disengage or de-couple the second pedicle screw 12 from the rod 14. The pedicle screws 10, 12 are no longer providing support and allow posterior movement. This will prevent stress shielding and reduce stresses on adjacent levels. Stress shielding refers to the reduction in bone density (osteopenia) as a result of removal of normal stress from the bone by an implant (for instance, the femoral component of a hip prosthesis). This is because by Wolff's law, bone in a healthy person or animal will remodel in response to the loads it is placed under. Therefore, if the loading on a bone decreases, the bone will become less dense and weaker because there is no stimulus for continued remodeling that is required to maintain bone mass.

This technology could be utilized to "decouple" the rod/screw interface to minimize or eliminate the stress shielding post fusion. This decoupling could provide the same benefit as surgical removal but without the need for a reoperation to remove the hardware post fusion. The stress shielding of the fused level may also contribute to adjacent level disease. If the screws/rods were decoupled, there is the possibility that the fused level would induce less stress on the adjacent level and minimize adjacent level disease. Once disengaged, an external magnetic field may be applied again to once again engage the second pedicle screw 12 to the rod 14, locking in a new configuration with a lower stress.

Alternatively, the device may be implanted into two vertebral bodies 10, 12 that have not been fused. This embodiment provides support and possible height restoration while the injured and/or diseased spinal segment heals. As healing occurs, the same or similar device can be used to introduce motion back to the spinal segment in the manner of an internal brace. If pain recurs, the surgeon can re-tighten pedicle screws to support the spine again. Initial implantation of the pedicle screws/rods can be set either rigid or flexible. The flexibility is adjusted post-operatively either increased or decreased based on the patient healing and pain levels.

Figure 2A:
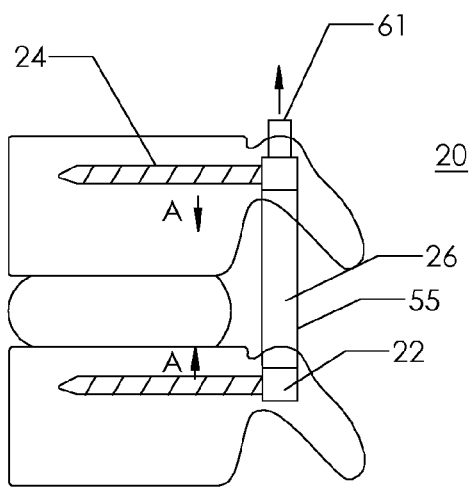
FIG. 2A illustrates another embodiment of a pedicle screw system for fusion applications.

FIGS. 2A and 2B illustrate another system 20 to control the loading of an interbody fusion to better promote fusion. Traditional pedicle screws may offload discs substantially. There is a general consensus in the medical community that fusion requires some degree of compression to fully form. The system 20 described herein includes two pedicle screws 22, 24 that are connected together via an adjustable rod 26.

The adjustable rod 26 is able to shorten (direction of facing arrows A) to apply a compressive load to the vertebral bodies to aid in fusion. The adjustable rod 26 may also be lengthened to reduce this compressive load. The system 20 may be adjusted repeatedly to apply multiple applications of a compressive load to the vertebral bodies if needed. For this system 20, interbody and pedicle screw fixation are conducted as normal, however, the two pedicle screws 22, 24 are interconnected to one another via the adjustable rod 26. The adjustable rod 26 includes an outer housing 55 that is secured to the pedicle screw 22 and includes a threaded shaft 53 that is fixedly secured to one end thereof and extends inwardly within the outer housing 55. The adjustable rod 26 further includes a hollow magnetic assembly 69 that is disposed within the outer housing 55 and includes a hollow magnetic element 45 disposed therein, the hollow magnetic assembly 69 having an internal threaded surface 51 engaged with external threads 73 of the threaded shaft 53, the magnetic assembly 69 being coupled to the other of the first pedicle screw and the second pedicle screw.

The hollow magnetic element 45 is preferably a radially-poled hollow magnet and effectuates rotation of the hollow magnetic assembly 69 that, for example, rotates in response to an externally applied moving magnetic field. The hollow magnetic assembly 69 may be formed by the hollow magnetic element 45 contained on or within a rotatable cylinder 47. The rotatable cylinder 47 has a hollow cavity 49 into or on which is bonded a nut 71 that contains the threaded surface 51. The nut 71 includes internal threads 51 that engage with a correspondingly threaded shaft 53 which is fixedly attached to the outer housing 55, for example, at weld joint 57. The outer diameter of the rotatable cylinder 47 may include an optional O-ring 59, which seals to the inner diameter of the outer housing 55. The rotatable cylinder 47 is longitudinally locked to the inner shaft 61 via a rotational coupling or swivel 63. A first pedicle screw 22 is attached to the outer housing 55 and a second pedicle screw 24 is attached to the inner shaft 61 during surgery. The inner shaft 61 is telescopically adjustable within the outer housing 55. The rotation of the radially-poled hollow magnetic element 45 contained in or on the rotatable cylinder 47 of the adjustable rod 26 is then translated into axial shortening or lengthening of the adjustable rod 26. A thrust bearing 65 is held between inner shaft 61 and rotatable cylinder 47, and supports the axial load if the adjustable rod 26 is adjusted in compression (applying distraction between vertebral bodies). An externally applied magnetic field may be applied using an external adjustment device of the type described herein.

Once implanted in the subject, if radiographic evidence of non-fusion or pseudo-fusion exists, then the surgeon can adjust the pressure on the fusion site by shortening the adjustable rod 26 and thereby moving the pedicle screws 22, 24 closer to one another to apply a compressive force between the vertebral bodies. The amount of shortening of the adjustable rod 26 will vary the degree of compression applied to the vertebral bodies. An alternative manner of assessing the degree of fusion is by supplying a strain gauge or other force measurement sensor on the adjustable rod, and non-invasively assessing the level of this force over time.

Figure 3:
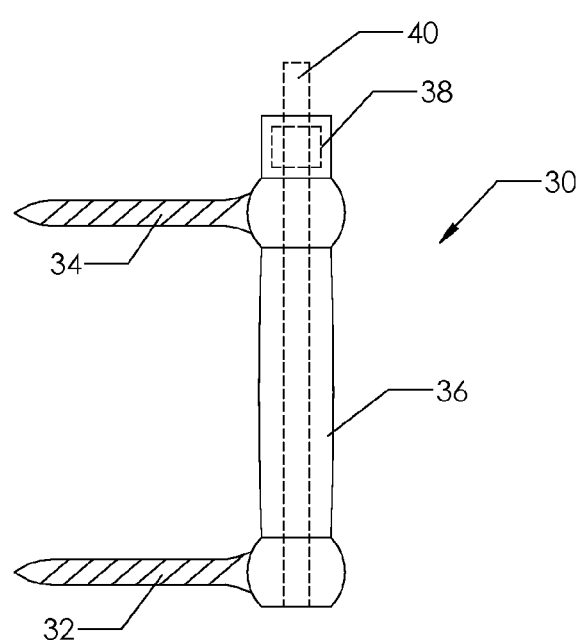
FIG. 3 illustrates another embodiment of a dynamic rod embodiment.

FIG. 3 illustrates another embodiment of a system 30 that includes two pedicle screws 32, 34 and a flexible body or spacer 36 that separates the two pedicle screws 32, 34. The flexible spacer 36 has at one end a magnetic element 38 that interfaces with a cord or rod 40 that extends within the flexible spacer 36. Movement of the magnetic element 38 (e.g., rotation) in response to an applied external magnetic field sets the tensions of the cord or rod 40 and pedicle screws 32, 34. Thus, the tension of the cord or rod 40 as well as the flexible spacer 36 can be controlled in a non-invasive manner. The tension on the cord or rod 40 may be adjusted by the externally applied magnetic field, in order to limit or delimit the amount of motion.

Figure 4A:
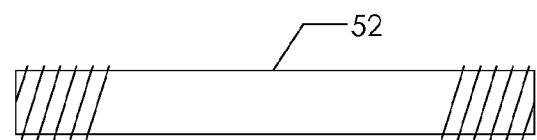
FIG. 4A illustrates a screw.
Figure 4B:
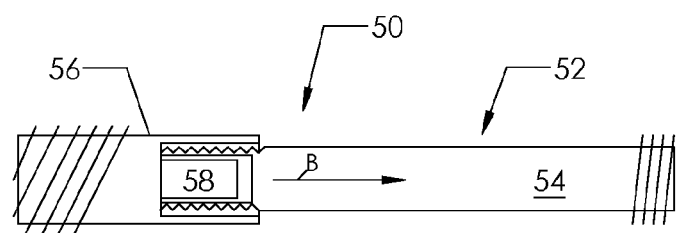
FIG. 4B illustrates an interbody device according to another embodiment.

FIG. 4B illustrates another embodiment of a system 50 that includes an adjustable screw 52 with threads on opposing ends much in the manner of a Herbert screw (FIG. 4A). The pitch of each threaded end is different from each other. In this embodiment, as seen in FIG. 4B, a single adjustable screw 52 includes a moveable segment or portion 54 that moves axially relative to a second segment or portion 56. An internal magnet 58 disposed in the adjustable screw 52 rotates in response to an applied external magnetic field thereby causing axial movement of the moveable segment 54 relative to the other portion 56. For example, the adjustable screw 52 can increase in length (arrow B), thereby creating distraction between vertebral bodies. The degree of distraction (or compression) can be altered as needed. This system 50 may be used in conjunction with fusion applications where adjustment is needed to apply compression or other forces to the fused vertebra. This is also useful in two level procedures to adjust one or both levels as this is very difficult to control using current devices and methods.

Figure 5:
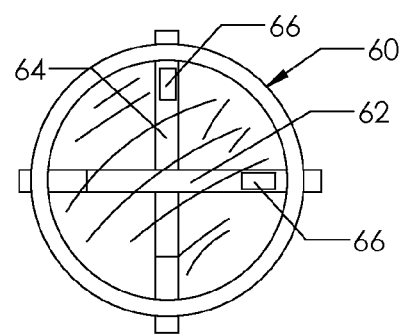
FIG. 5 illustrates an artificial disc embodiment.

FIG. 5 illustrates another embodiment of an artificial disc 60 that is adjustable in two directions. A significant effort has gone on into the development of artificial discs. A key design feature of almost all artificial discs is to mimic the natural motion of the spine. A critical feature of artificial discs is the center of rotation (COR) and where it is located. While much work has gone into precisely calculating the COR of implants, in practice, trying to place the artificial disc and lining up the COR is nearly impossible. Quite often the surgeon has missed placement, either lateral/medial and/or anterior/posterior. This misplacement is very difficult or impossible to correct.

There is a need post-implantation of an artificial disc to adjust the COR. FIG. 5 illustrates one such artificial disc 60 that includes an x-y adjustment feature built therein. The adjustment feature includes two orthogonal adjustment members 62, 64 that are able to move the body of the artificial disc 60 in the x and y directions. The adjustment members may lengthen or shorten based on a rotational magnet 66 contained in each adjustment member. Application of an external magnetic field is able to adjust each adjustment member. Preferably, each adjustment member can be independently adjusted by a single external adjustment device.

Ideally, the adjustment would be done with the aid of a fluoroscope. The medial to lateral positioning is relatively straight forward and can be done while the patient is in a standing position. For the A/P positioning, the patient could go through flexion and extension motion and the surgeon can monitor the movement of the vertebra relative to the disc and adjust accordingly. This would ensure ideal alignment of the COR of the implant.

Figure 6:
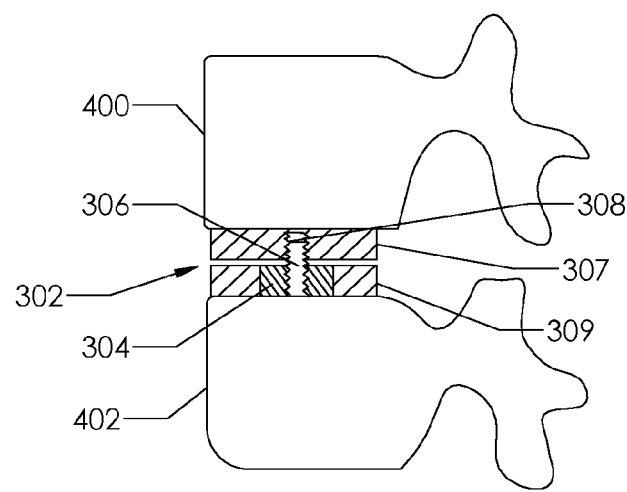
FIG. 6 illustrates one embodiment of a distraction device used for vertebral body height adjustment.

FIG. 6 illustrates a distraction device 302 configured for distraction between a first vertebral body 400 and a second vertebral body 402. Intervertebral disks can degenerate, bulge, herniate or thin, and cause accompanying back pain. In this embodiment, the distraction device 302 is inserted between adjacent vertebral bodies 400, 402 and using an external adjustment device (described below) is used to adjust the height of the distraction device 302 to the desired level. This distraction device 302 can distract the vertebral body (e.g., vertebral body 400) to the correct height. Subsidence is a common problem resulting in the loss of disc height over time. After implantation, the distraction device 302 can be adjusted post-operatively using an external adjustment device to restore disc height. The adjustments may be performed intermittently or periodically as required. The adjustments are preferably made after implantation but prior to complete fusion of the affected vertebral bodies.

Figure 13:
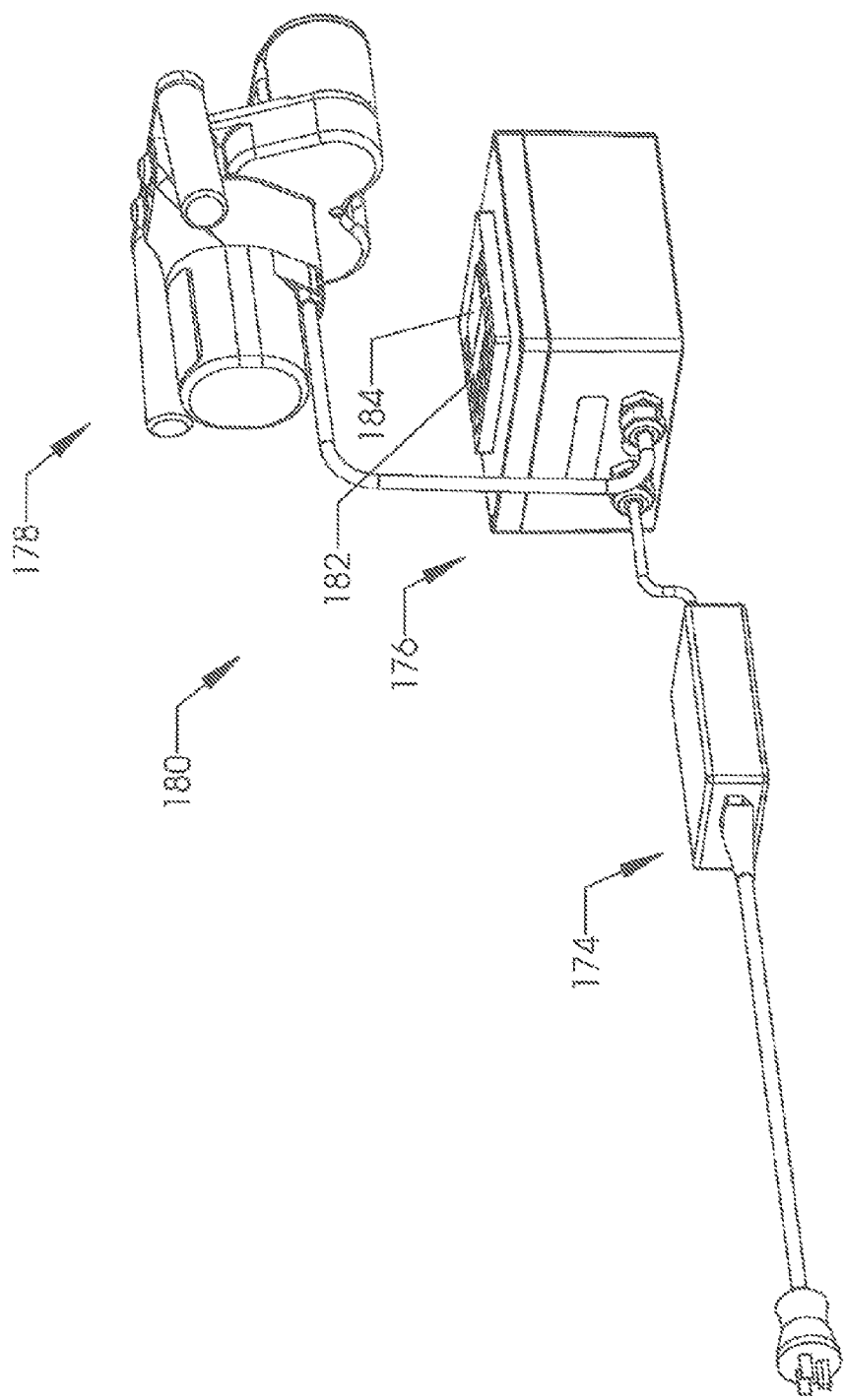
FIG. 13 illustrates a perspective view of an external adjustment device.
Figure 14:
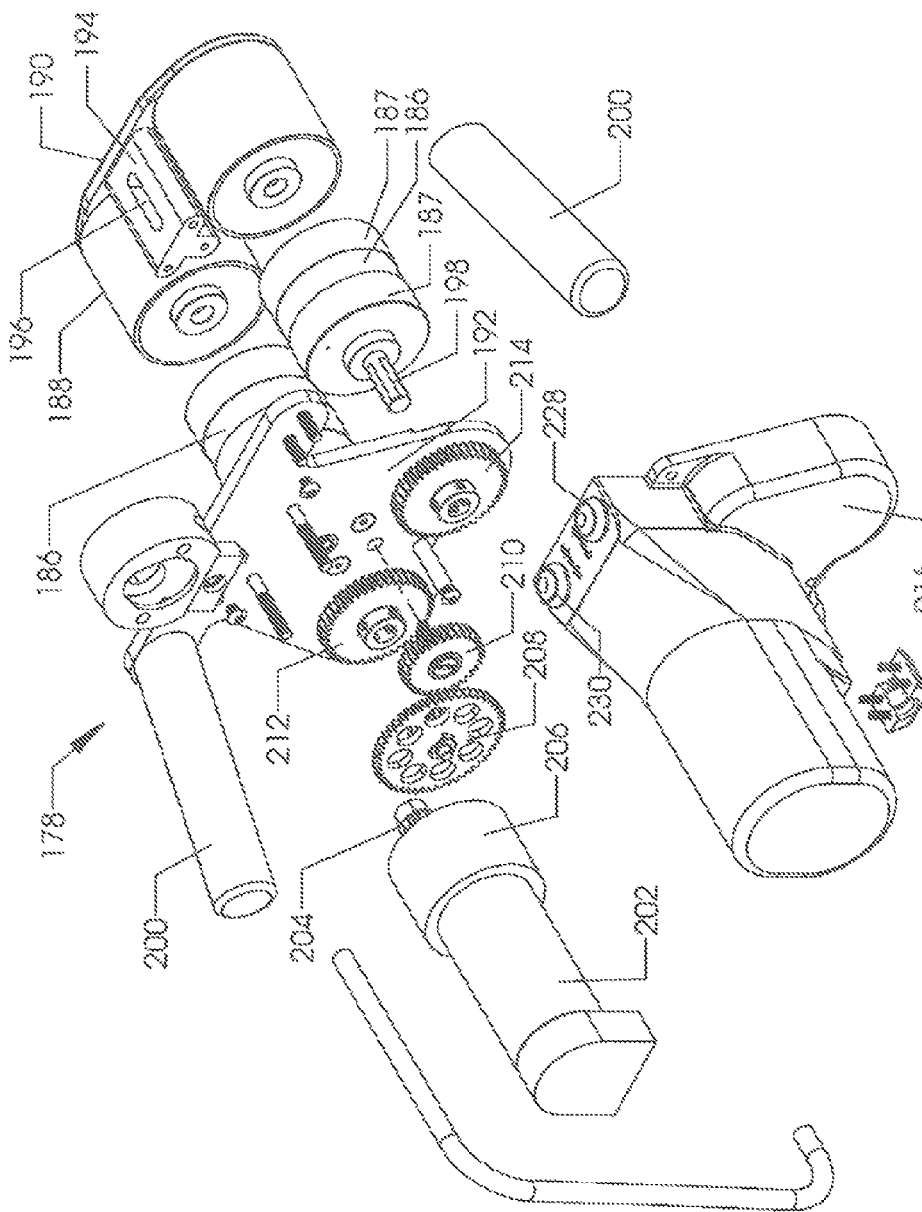
FIG. 14 illustrates an exploded view of the magnetic handpiece of the external adjustment device of FIG. 13.

The distraction device 302 contains a first portion 307 and a second portion 309 and an internal, permanent magnet 304 that can be rotated in response to an applied external magnetic field via an external adjustment device 180 as seen in FIGS. 13 and 14. internal magnet 304 is coupled to lead screw 306 so that rotation motion changes the displacement between lead screw 306 and the female thread 308 inside the first portion 307 of the distraction device 302 (although the configuration could be reversed). Rotation of the lead screw 306 in one direction causes the first portion 307 and the second portion 309 to separate from one another, thereby increasing the height between the same and the attached vertebral bodies 400, 402. Rotation of the lead screw 306 in the opposite direction causes the first portion 307 and the second portion 309 to move closer together, thereby decreasing the height between the same and the attached vertebral bodies 400, 402.

Figure 7:
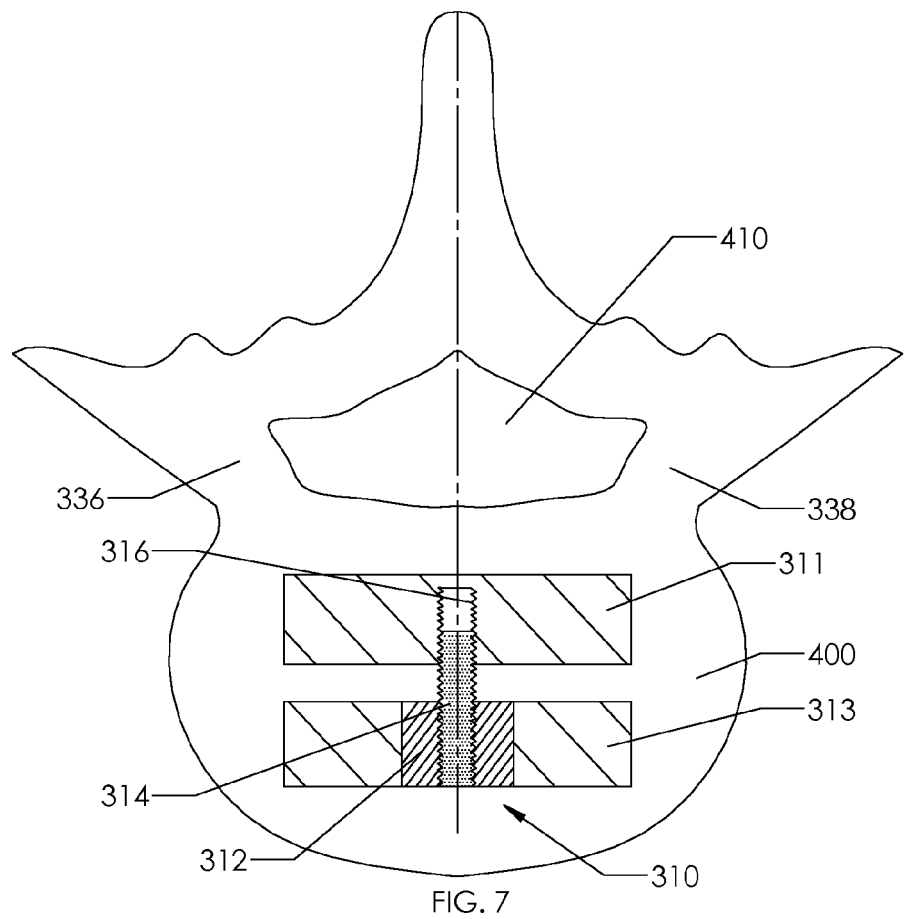
FIG. 7 illustrates a top view of one embodiment of a distraction device used for vertebral body width adjustment.
Figure 8:
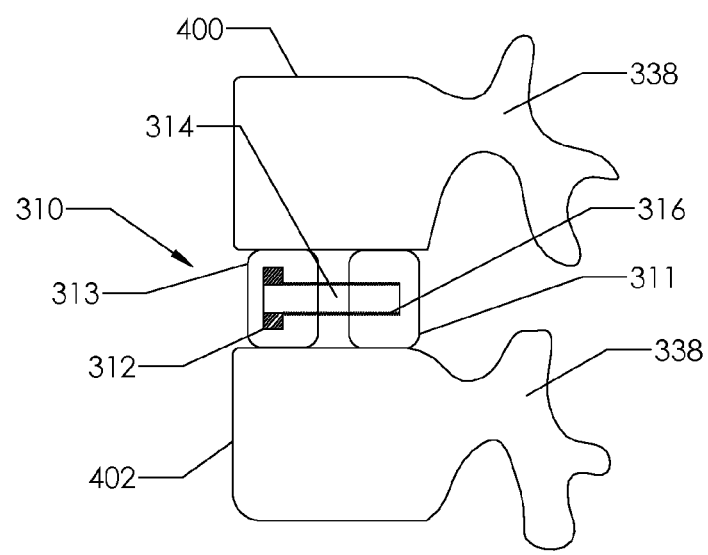
FIG. 8 illustrates a side view of the embodiment of FIG. 7.

FIGS. 7 and 8 illustrate another embodiment of a distraction device 310. This embodiment of the distraction device 310 is used for width adjustment. A wider interbody device provides better clinical results by providing additional stability and minimizing subsidence issues. In this embodiment, the distraction device 310 has a fixed height but can be distracted using an external adjustment device 180 like that seen in FIGS. 13 and 14 to provide a variable width. The distraction device 310 of FIGS. 7 and 8 is oriented between a first vertebral body 400 and a second vertebral body 402, as best seen in FIG. 8, and is generally perpendicular with the orientation of the device 302 of FIG. 6. Distraction of the device 310 will expand the width between the vertebral bodies 400, 102. Like the prior embodiment, there is a first portion 311 and a second portion 313 and an internal, permanent magnet 312 that can be rotated in response to an applied external magnetic field via an external adjustment device 180. The internal magnet 312 is coupled to a lead screw 314 so that rotational motion changes displacement between lead screw 314 and a female thread 316 located inside the first portion 311 of the distraction device 310. The distraction device 310 has a fixed height which provides for a small interbody implant to be inserted. However, the adjustability of the width of the distraction device 310 and the vertebral bodies 400, 402 containing the same provides for increased stability. Also illustrated are pedicles 336, 338 and the spinal canal 410. The distraction device 310 generally distracts in a direction that is substantially perpendicular to the longitudinal axis of the spinal canal 410.

Figure 9:
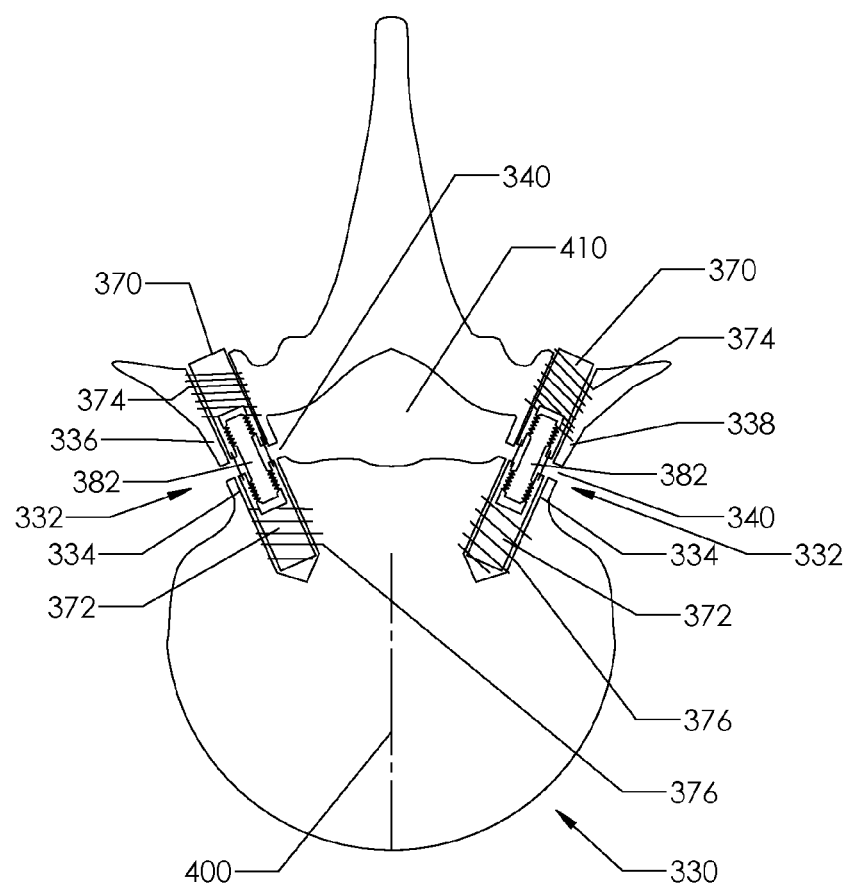
FIG. 9 illustrates an embodiment of a system that includes multiple distraction devices for the selective and incremental expansion of the spinal column.

FIG. 9 illustrates another embodiment of a system 330 that includes multiple distraction devices 332 for the selective and incremental expansion of the spinal canal 410. In this embodiment, two distraction devices 332 are located within respective bores 334 formed in each pedicle 336, 338 of a single vertebral body 400. The bores 334 may be formed using conventional drilling tools and techniques. After the bores 334 have been formed, circumferential pedicle cuts 340 are made in each pedicle 336, 338 (i.e., osteotomy). The circumferential pedicle cuts 340 are made by a rotating cutting tool such as a burr (not shown) that is placed within each bore 334. The circumferential pedicle cuts 340, once made, completely separate a portion of the vertebral body 400 from the respective pedicles 336, 338. The two distraction devices 332 are secured within the respective bores 334. The distraction devices 332 may be secured using an adhesive, cement, threads that engage bone tissue or fasteners (e.g., screws or the like).

Utilizing the Ilizarov technique of bone lengthening, only a small gap in each pedicle 336, 338 is left after installation of the distraction devices 332. As the cut pedicles 336, 338 begin to grow back together, each distraction device 332 is expanded incrementally at a rate of approximately one (1) millimeter per day. Each incremental expansion of the distraction devices 332 progressively opens up the spinal canal 410. This is accomplished using the external adjustment device 180 described herein. The adjustments are performed while the subject is awake to provide feedback regarding symptom relief. For example, after adjustment, the subject may move his or her spine through one or more motions to determine the degree to which expansion of the spinal canal 410 has reduced discomfort or pain. Additional adjustments of the distraction devices 332 may be made daily or periodically until the spinal canal 410 has been opened up enough to provide the subject with the desired amount of pain or discomfort relief. As part of the periodic adjustment, the subject may go through one or more range of motions to give direct feedback on pain and discomfort levels. Once the desired endpoint has been reached, additional adjustments can be stopped, at which point the cut pedicles 336, 338 will undergo a period of consolidation and fully form into a solid bone mass. FIG. 9 illustrates distraction devices 332 of the type illustrated in FIG. 12 secured within bores 34, although other distraction devices 332 may be used in connection with the procedure.

Figure 10:
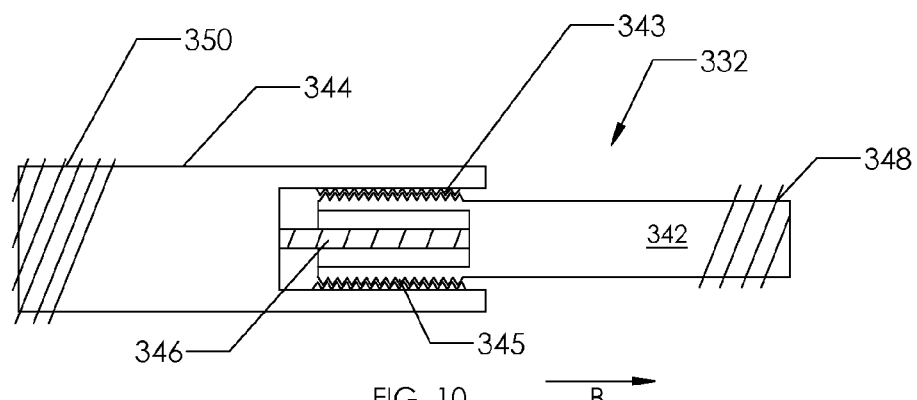
FIG. 10 illustrates an embodiment of one type of distraction device.

FIG. 10 illustrates one embodiment of a distraction device 332 that includes a moveable segment or portion 342 that moves axially relative to a second segment or portion 344. An axially-poled internal magnet 346 disposed in the distraction device 332 rotates in response to an applied external magnetic field thereby causing axial movement of the moveable segment 342 relative to the other portion 344. The moveable segment 342 contains threads 343 on a portion thereof that interface with corresponding threads 345 disposed on the second portion 344. Rotation of the moveable segment 42 relative to the second portion 44 results in axial displacement of the distraction device 332. For example, the distraction device 332 can increase in length (arrow B), thereby creating a distraction force. The degree of distraction (or compression) can be altered as needed. Threads 348, 350 are located at the respective ends of the moveable segment 342 and the second portion 344 which can be used to engage bone tissue.

Figure 11:
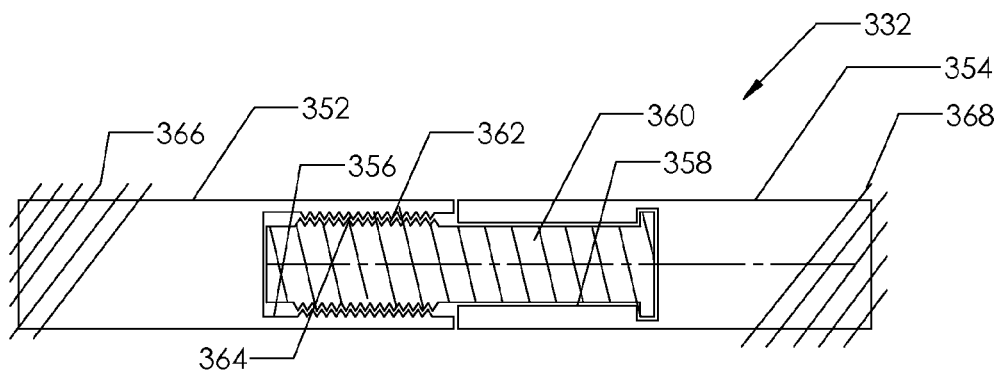
FIG. 11 illustrates an embodiment of another type of distraction device.

FIG. 11 illustrates another embodiment of a distraction device 332. The distraction device 332 includes first and second portions 352, 354 that include respective recesses 356, 358 that contain a rotatable, axially-poled permanent magnet 360. The permanent magnet 360 is coupled to or may include a threaded portion 362 that engages with corresponding threads 364 in one of the first and second portions 352, 354. Rotation of the rotatable permanent magnet 360 extends the first and second portions 352, 354 away from one another, thereby increasing the distraction force. As seen in FIG. 11, the ends of the first and second portions 352, 354 may include threads 366, 368 which can be used to engage bone tissue within each bore 334.

Figure 12:
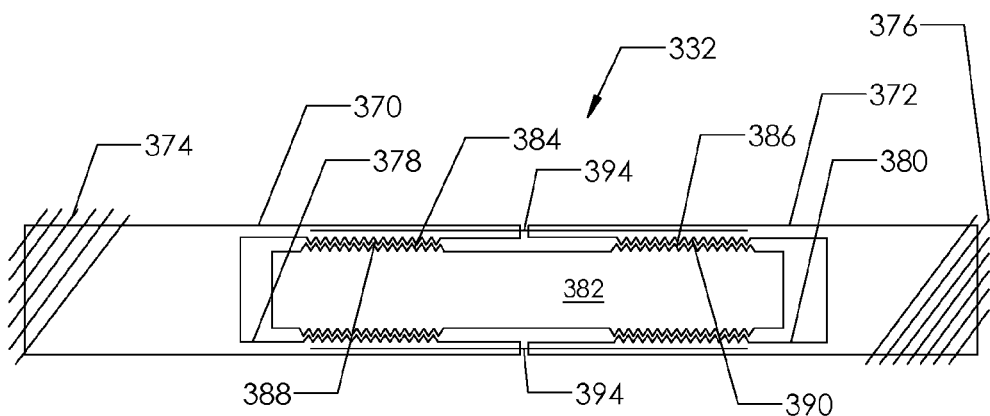
FIG. 12 illustrates an embodiment of another type of distraction device. Two of these devices are illustrated in the system of FIG. 9.

FIG. 12 illustrates another embodiment of a distraction device 332. The distraction device 332 includes first and second portions 370, 372 each having respective threads 374, 376 at an end thereof for mounting the distraction device 332 within each bore 334 as described above. The first and second portions 370, 372 include respective recesses 378, 380 that contain a rotatable permanent magnet 382. The permanent magnet 382 is coupled to or may include two threaded portions 384, 386 that engage with corresponding threads 388, 390 in the first and second portions 370, 372. In the embodiment of FIG. 12, the distraction device 332 includes one or more guides 394 that extend between the first and second portions 370, 372. The guides 394 prevent relative rotation between the first and second portions 370, 372 yet still permit elongation of the distraction device 332. For example, a plurality of guides 394 could be located circumferentially about the first and second portions 370, 372 to prevent relative rotation.

FIG. 13 illustrates an external adjustment device 180 which is used to non-invasively adjust the devices and systems described herein. The external adjustment device 180 includes a magnetic handpiece 178, a control box 176 and a power supply 174. The control box 176 includes a control panel 182 having one or more controls (buttons, switches or tactile, motion, audio or light sensors) and a display 184. The display 184 may be visual, auditory, tactile, the like or some combination of the aforementioned features. The external adjustment device 180 may contain software which allows programming by the physician.

FIG. 14 shows the detail of the magnetic handpiece 178 of the external adjustment device 180. As seen in FIG. 14, there are two (2) magnets 186 that have a cylindrical shape. The magnets 186 are made from rare earth magnets. The magnets 186 are bonded or otherwise secured within magnetic cups 187. The magnetic cups 187 include a shaft 198 which is attached to a first magnet gear 212 and a second magnet gear 214, respectively. The orientation of the poles of each the two magnets 186 are maintained in relation to each other by means of the gearing system (by use of center gear 210, which meshes with both first magnet gear 212 and second magnet gear 214).

The components of the magnetic handpiece 178 are held together between a magnet plate 190 and a front plate 192. Most of the components are protected by a cover 216. The magnets 186 rotate within a static magnet cover 188, so that the magnetic handpiece 178 may be rested directly on the patient, while not imparting any motion to the external surfaces of the patient Prior to distracting the intramedullary lengthening device 110, the operator places the magnetic handpiece 178 over the patient near the location of the cylindrical magnet 134. A magnet standoff 194 that is interposed between the two magnets 186 contains a viewing window 196 to aid in the placement. For instance, a mark made on the patient's skin at the appropriate location with an indelible marker may be viewed through the viewing window 196. To perform a distraction, the operator holds the magnetic handpiece 178 by its handles 200 and depresses a distract switch 228, causing motor 202 to drive in a first direction. The motor 202 has a gear box 206 which causes the rotational speed of an output gear 204 to be different from the rotational speed of the motor 202 (for example, a slower speed). The output gear 204 then turns a reduction gear 208 which meshes with center gear 210, causing it to turn at a different rotational speed than the reduction gear 208. The center gear 210 meshes with both the first magnet gear 212 and the second magnet gear 214 turning them at a rate which is identical to each other. Depending on the portion of the body where the magnets 186 of the external adjustment device 180 are located, it is desired that this rate be controlled, to minimize the resulting induced current density imparted by magnet 186 and cylindrical magnet 134 though the tissues and fluids of the body. For example, a magnet rotational speed of 60 RPM or less is contemplated although other speeds may be used, such as 35 RPM or less. At any time, the distraction may be lessened by depressing the retract switch 230. For example, if the patient feels significant pain, or numbness in the area holding the device.

FIGS. 15 and 16 illustrate the progression of the magnets 186 (individually numbered 1134 and 1136) and the implanted magnet 1064 that is located within the distraction device during use. Implanted magnet 1064 is shown for illustration purposes. Implanted magnet 1064 is one possible embodiment of the magnetic element described herein. FIGS. 15 and 16 illustrate the external adjustment device 180 being disposed against the external surface of the patient's skin 1180 adjacent the spine. In the non-invasive adjustment procedure depicted, the patient 100 lies in a prone position, and the external adjustment device 180 is placed upon the patient's back. However, the adjustment is conceived possible with the patient in supine or standing positions. The external adjustment device 180 is placed against the skin 1180 in this manner to remotely rotate the implanted magnet 1064. As explained herein, rotation of the implanted magnet 1064 is translated into linear motion to controllably adjust the distraction device.

As seen in FIGS. 15 and 16, the external adjustment device 180 may be pressed down on the patient's skin 1180 with some degree of force such that skin 1180 and other tissue, such as the underlying layer of fat 1182, are pressed or forced into the recess 1174 of the external adjustment device 180. FIGS. 15 and 16 show the magnetic orientation of the implanted magnet 1064 as it rotates in response to rotation of the permanent magnets 1134, 1136 of the external adjustment device 180.

With reference to FIG. 15, the implanted magnet 1064 is shown being oriented with respect to the two permanent magnets 1134, 1136 via an angle θ. This angle θ may depend on a number of factors including, for instance, the separation distance between the two permanent magnets 1134, 1136, the location or depth of where the implanted magnet 1064 is located, the degree of force at which the external adjustment device 180 is pushed against the patient's skin. Generally, in applications including some obese patients, the angle θ should be at or around 90° to achieve maximum drivability (e.g., torque).

FIG. 15 illustrates the initial position of the two permanent magnets 1134, 1136 and the implanted magnet 1064. This represents the initial or starting location (e.g., position as indicated). Of course, it should be understood that, during actual use, the particular orientation of the two permanent magnets 1134, 1136 and the implanted magnet 1064 will vary and likely will not have the starting orientation as illustrated in FIG. 15. In the starting location illustrated in FIG. 15, the two permanent magnets 1134, 1136 are oriented with their poles in an N-S/S-N arrangement. The implanted magnet 1064 is, however, oriented generally perpendicular to the poles of the two permanent magnets 1134, 1136.

FIG. 16 illustrates the orientation of the two permanent magnets 1134, 1136 and the implanted magnet 1064 after the two permanent magnets 1134, 1136 have rotated through 90°. The two permanent magnets 1134, 1136 rotate in the direction of arrow A (e.g., clockwise) while the implanted magnet 1064 rotates in the opposite direction (e.g., counter clockwise) represented by arrow B. It should be understood that the two permanent magnets 1134, 1136 may rotate in the counter clockwise direction while the implanted magnet 1064 may rotate in the clockwise direction.

During operation of the external adjustment device 180, the permanent magnets 1134, 1136 may be driven to rotate the implanted magnet 1064 through one or more full rotations in either direction to increase or decrease distraction of the device as needed. Of course, the permanent magnets 1134, 1136 may be driven to rotate the implanted magnet 1064 through a partial rotation as well (e.g., ¼, ⅛, ¹⁄₁₆, etc.). The use of two magnets 1134, 1136 is preferred over a single external magnet because the implanted magnet 1064 may not be oriented perfectly at the start of rotation, so one external magnet 1134, 1136 may not be able to deliver its maximum torque, which depends on the orientation of the internal driven magnet 1064 to some degree. However, when two (2) external magnets (1134, 1136) are used, one of the two, 1134 or 1136, will have an orientation relative to the internal driven magnet 1064 that is better or more optimal than the other. In addition, the torques imparted by each external magnet 1134, 1136 are additive.

While embodiments of the present invention have been shown and described, various modifications may be made without departing from the scope of the present invention. As one example, the devices described herein may be used to lengthen or reform a number of other bones such as the mandible or the cranium. The invention, therefore, should not be limited, except to the following claims, and their equivalents.

What is claimed is:

1. A system comprising:
    a first pedicle screw;
    a second pedicle screw separated from the first pedicle screw by a distance; and
    an adjustable rod comprising:
        an outer housing configured to affix to the first pedicle screw, the outer housing having a threaded shaft secured to one end thereof and extending along an interior portion thereof;
        an inner shaft configured to affix to the second pedicle screw, at least a portion of the inner shaft being telescopically adjustable within the outer housing; and
        a hollow magnetic assembly disposed at least partially within the outer housing and comprising a hollow magnetic element disposed around at least a portion of the threaded shaft, the hollow magnetic assembly having an internal threaded surface configured to engage the threaded shaft,
    wherein the hollow magnetic assembly is rotatably coupled to the inner shaft by a rotational coupling;
    wherein the hollow magnetic assembly is configured to rotate in response to an externally applied magnetic field, thereby increasing or decreasing the distance between the first pedicle screw and the second pedicle screw.

2. The system of claim 1, wherein the hollow magnetic assembly comprises a hollow cylindrical radially-poled magnet.

3. The system of claim 2, wherein the hollow cylindrical radially-poled magnet comprises a rare earth magnet.

4. The system of claim 2, wherein the internal threaded surface of the hollow magnetic assembly comprises a nut coupled to an internal surface of the hollow magnetic assembly.

5. The system of claim 1, further comprising a thrust bearing disposed between the hollow magnetic assembly and the second pedicle screw.

6. The system of claim 1, further comprising an external adjustment device configured to apply a rotating magnetic field.

7. The system of claim 1, wherein the hollow magnetic assembly further comprises the hollow magnetic element contained on or within a rotatable cylinder, the rotatable cylinder having a hollow cavity therein.

8. The system of claim 7, wherein the hollow cavity further comprises a nut affixed thereto, wherein the nut comprises the internal threaded surface configured to engage the threaded shaft.

9. The system of claim 7, wherein an outer diameter of the rotatable cylinder comprises an o-ring configured to seal to an inner diameter of the outer housing.

10. The system of claim 1, wherein the threaded shaft is secured to a first end of the outer housing, and extends toward a second end of the outer housing within the interior portion thereof.

11. The system of claim 10, wherein the first end of the outer housing is configured to affix to the first pedicle screw.

12. The system of claim 1, wherein the rotational coupling is configured to longitudinally lock the hollow magnetic assembly to the inner shaft.

13. The system of claim 1, wherein a rotation of the hollow magnetic assembly in a first direction is configured to cause the adjustable rod to lengthen, and a rotation of the hollow magnetic assembly in a second direction opposite the first direction is configured to cause the adjustable rod to shorten.

14. The system of claim 1, wherein the rotational coupling comprises a swivel.

15. The system of claim 1, wherein the hollow magnetic assembly is configured to threadably engage the threaded shaft.

16. A system comprising:
a first pedicle screw;
a second pedicle screw;
an adjustable rod comprising:
  an outer housing coupled to the first pedicle screw, the outer housing having a threaded shaft extending along an interior portion thereof;
  an inner shaft coupled to the second pedicle screw, at least a portion of the inner shaft telescopically adjustable within the outer housing;
  a hollow magnetic assembly comprising a hollow magnetic element disposed therein, the hollow magnetic element disposed around at least a portion of the threaded shaft, the hollow magnetic assembly having an internal threaded surface configured to engage the threaded shaft, the hollow magnetic assembly being rotatably coupled to the second pedicle screw by a rotational coupling; and
  a thrust bearing disposed between the magnetic assembly and the second pedicle screw,
wherein the hollow magnetic assembly rotates in response to an externally applied magnetic field to thereby lengthen or shorten a distance between the first pedicle screw and the second pedicle screw,
wherein the hollow magnetic assembly is configured to threadably engage the threaded shaft.

17. The system of claim 16, wherein the internal threaded surface of the hollow magnetic assembly comprises a nut coupled to an internal surface of the hollow magnetic assembly.

18. The system of claim 16, wherein the external magnetic field comprises a rotating magnetic field.

19. The system of claim 16, wherein an outer diameter of the hollow magnetic assembly comprises an o-ring configured to seal to an inner diameter of the outer housing.

* * * * *